(12) United States Patent
Lampropoulos et al.

(10) Patent No.: US 10,792,465 B2
(45) Date of Patent: Oct. 6, 2020

(54) QUICK-RELEASE HUBS FOR MEDICAL DEVICES

(71) Applicant: Merit Medical Systems, Inc., South Jordan, UT (US)

(72) Inventors: Justin Lampropoulos, Lehi, UT (US); Brian Stevens, Pleasant Grove, UT (US); Richard Jenkins, Bluffdale, UT (US); Gregory R. McArthur, Sandy, UT (US)

(73) Assignee: Merit Medical Systems, Inc., South Jordan, UT (US)

( * ) Notice: Subject to any disclaimer, the term of this patent is extended or adjusted under 35 U.S.C. 154(b) by 43 days.

(21) Appl. No.: 15/152,870

(22) Filed: May 12, 2016

(65) Prior Publication Data

US 2016/0331929 A1  Nov. 17, 2016

Related U.S. Application Data

(60) Provisional application No. 62/162,302, filed on May 15, 2015.

(51) Int. Cl.
| | | |
|---|---|---|
| *A61M 25/00* | (2006.01) | |
| *A61M 39/10* | (2006.01) | |
| *A61M 29/00* | (2006.01) | |
| *A61M 25/06* | (2006.01) | |

(52) U.S. Cl.
CPC ........ *A61M 25/0097* (2013.01); *A61M 39/10* (2013.01); *A61M 29/00* (2013.01); *A61M 2025/0681* (2013.01); *A61M 2039/1027* (2013.01)

(58) Field of Classification Search
CPC .. A61M 2025/0681; A61M 2039/1027; A61M 25/0097; A61M 29/00; A61M 39/10
See application file for complete search history.

(56) References Cited

U.S. PATENT DOCUMENTS

| | | | |
|---|---|---|---|
| 3,406,685 A | 10/1968 | May | |
| 4,698,056 A | 10/1987 | Ciannella | |
| 4,840,622 A | 6/1989 | Hardy | |
| 5,098,392 A | 3/1992 | Fleischhacker et al. | |
| 5,205,830 A | 4/1993 | Dassa et al. | |
| 5,334,157 A * | 8/1994 | Klein ............... | A61M 25/0637 604/160 |

(Continued)

FOREIGN PATENT DOCUMENTS

| | | |
|---|---|---|
| EP | 2633828 | 9/2013 |
| JP | 2003265618 | 9/2003 |
| WO | 2008131289 | 10/2008 |

OTHER PUBLICATIONS

International Search Report and Written Opinion dated Sep. 1, 2016 for PCT/US2016/032010.

(Continued)

*Primary Examiner* — Quynh-Nhu H. Vu
(74) *Attorney, Agent, or Firm* — Stoel Rives LLP

(57) ABSTRACT

Hub assemblies that include a first hub and a second hub can be used to selectively couple and uncouple medical device components to and from each other without rotating the first hub relative to the second hub. Some hub assemblies can include a dilator that includes a dilator hub and an introducer sheath that includes an introducer sheath hub.

11 Claims, 15 Drawing Sheets

(56) References Cited

U.S. PATENT DOCUMENTS

| | | | |
|---|---|---|---|
| 5,336,191 A * | 8/1994 | Davis | A61B 10/0283 |
| | | | 604/165.01 |
| 6,053,904 A | 4/2000 | Scribner et al. | |
| 6,336,914 B1 * | 1/2002 | Gillespie, III | A61M 25/0606 |
| | | | 604/165.01 |
| 6,368,301 B1 | 4/2002 | Hamilton et al. | |
| 6,520,938 B1 * | 2/2003 | Funderburk | A61M 25/0097 |
| | | | 604/162 |
| 6,607,511 B2 | 8/2003 | Halseth et al. | |
| 7,922,696 B2 * | 4/2011 | Tal | A61M 25/0097 |
| | | | 604/165.01 |
| 8,177,770 B2 * | 5/2012 | Rasmussen | A61M 25/0097 |
| | | | 604/523 |
| 8,579,805 B2 | 11/2013 | Accisano, III | |
| 2002/0010437 A1 * | 1/2002 | Lopez | A61M 39/1011 |
| | | | 604/256 |
| 2002/0072712 A1 | 6/2002 | Nool et al. | |
| 2003/0028182 A1 * | 2/2003 | Abboud | A61B 18/02 |
| | | | 606/21 |
| 2003/0050611 A1 | 3/2003 | Cindrich | |
| 2003/0171718 A1 * | 9/2003 | DeLegge | A61B 17/3415 |
| | | | 604/164.01 |
| 2005/0004523 A1 | 1/2005 | Osborne et al. | |
| 2006/0052750 A1 | 3/2006 | Lenker et al. | |
| 2006/0135973 A1 | 6/2006 | Hawkins et al. | |
| 2009/0048485 A1 | 2/2009 | Heisler | |
| 2011/0127767 A1 * | 6/2011 | Wicks | F16L 37/56 |
| | | | 285/319 |
| 2013/0150793 A1 | 6/2013 | Beissel et al. | |
| 2016/0367793 A1 * | 12/2016 | Andreen | A61M 39/105 |

OTHER PUBLICATIONS

International Preliminary Report dated Nov. 21, 2017 for PCT/US2016/032010.
European Search Report dated Dec. 11, 2018 for EP16796969.0.

* cited by examiner

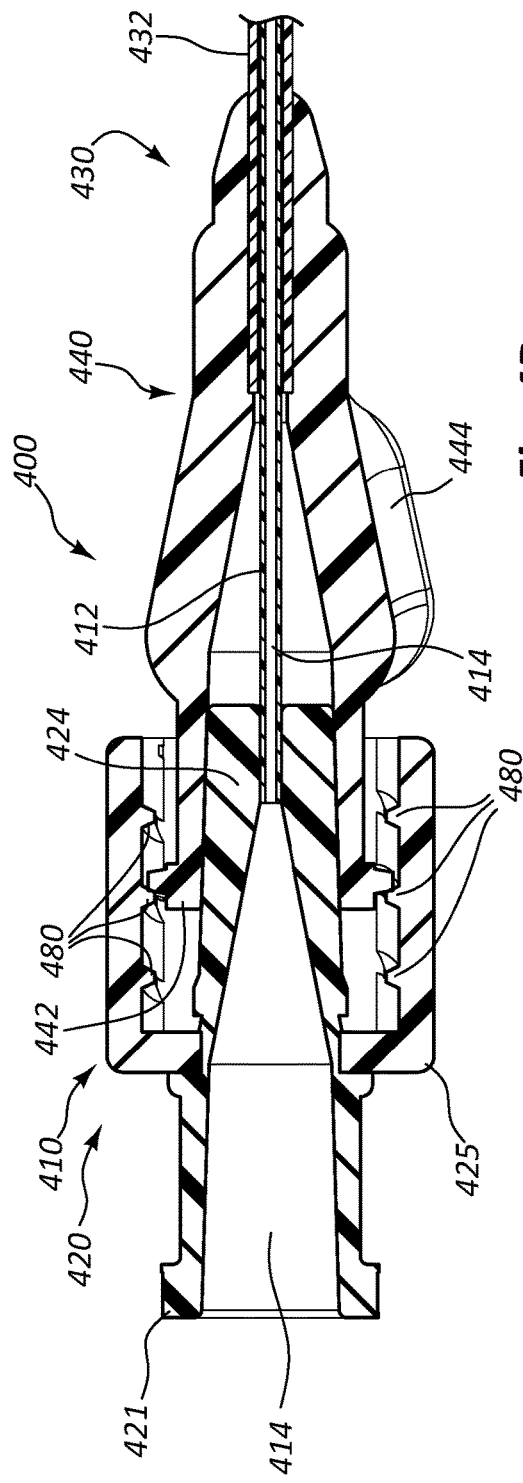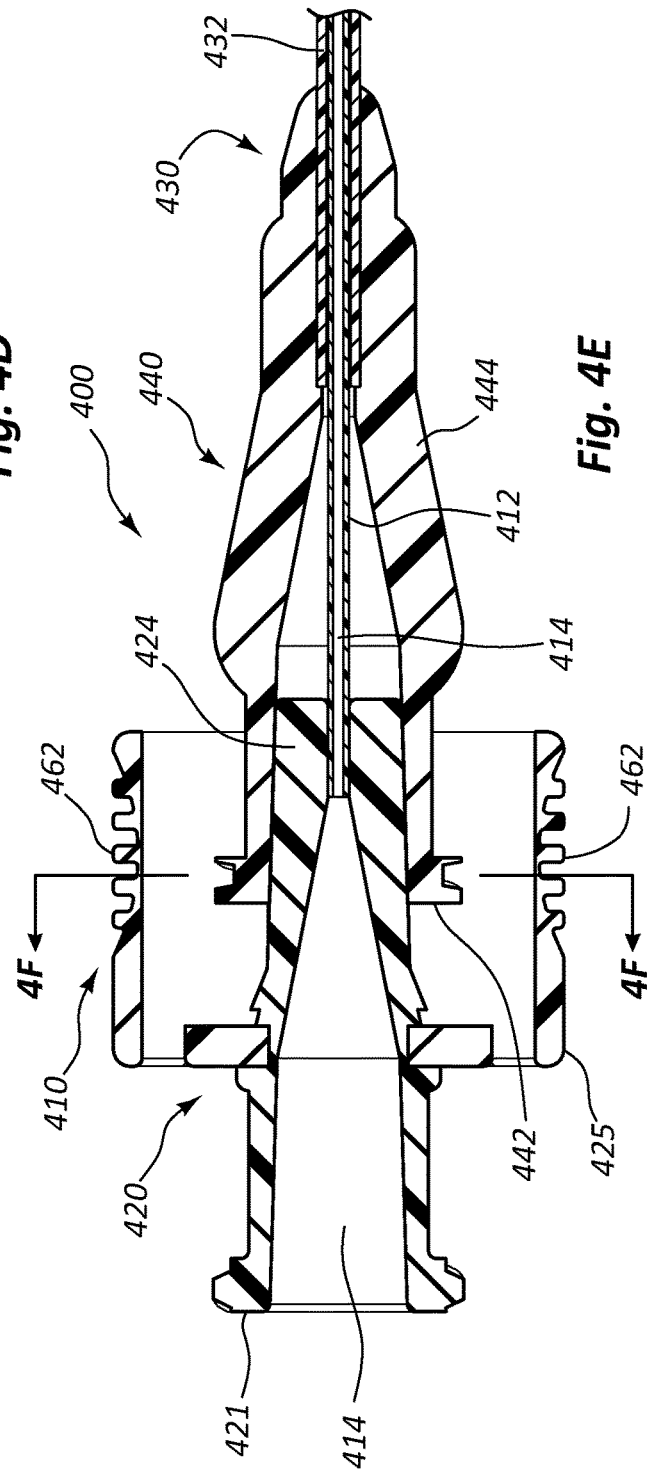

QUICK-RELEASE HUBS FOR MEDICAL DEVICES

RELATED APPLICATIONS

This application claims priority to U.S. Provisional Application No. 62/162,302 filed on May 15, 2015 and titled, "Quick-Release Hubs for Medical Devices," which is hereby incorporated by reference in its entirety.

TECHNICAL FIELD

The present disclosure relates generally to the field of medical devices. More specifically, the present disclosure relates to hubs and hub assemblies that can be used to couple components of a medical device or assembly to one another. Related methods are also disclosed.

BRIEF DESCRIPTION OF THE DRAWINGS

The written disclosure herein describes illustrative embodiments that are non-limiting and non-exhaustive. Reference is made to certain of such illustrative embodiments that are depicted in the figures, in which:

FIG. 4D is a cross-sectional view of the assembled introducer sheath hub assembly of FIG. 4A.

FIG. 4E is another cross-sectional view of the assembled introducer sheath hub assembly of FIG. 4A.

DETAILED DESCRIPTION

This disclosure broadly relates to hubs, hub assemblies, and introducer sheath assemblies for medical devices, along with related methods. Certain embodiments relate, more particularly, to introducer sheath assemblies that allow a practitioner to selectively couple and/or uncouple a dilator hub to and/or from an introducer sheath hub.

The components of the embodiments as generally described and illustrated in the figures herein can be arranged and designed in a wide variety of different configurations. Thus, the following more detailed description of various embodiments, as represented in the figures, is not intended to limit the scope of the present disclosure, but is merely representative of various embodiments. While various aspects of the embodiments are presented in drawings, the drawings are not necessarily drawn to scale unless specifically indicated.

The directional terms "proximal" and "distal" are generally given their ordinary meanings in the art. That is, the distal end of a device or component is the end of the component that is furthest from the practitioner during ordinary use. The proximal end refers to the opposite end, or the end nearest the practitioner during ordinary use.

Introducer sheath assemblies may be used to facilitate the introduction of a medical device, such as a guidewire or catheter, into the vasculature or other body cavity of a patient. In an exemplary procedure, a needle (e.g., a small gauge needle) may be used to create an initial access puncture into the patient's vasculature. A guidewire (e.g., a small diameter guidewire) may then be threaded through the needle. Once the guidewire has been properly placed, the needle used to access the patient's vasculature may then be withdrawn from the patient. An introducer sheath assembly is then threaded over the guidewire and inserted into the patient. The introducer sheath assembly can include an introducer sheath and a dilator that is positioned inside the introducer sheath. The dilator may impart increased stiffness to the introducer sheath, thereby facilitating insertion of the introducer sheath into the patient. Stated differently, the pliant nature of the introducer sheath may make it difficult to introduce the introducer sheath into the vasculature of the patient without a stiffening dilator. Once the introducer sheath is properly positioned within the patient, the dilator may be uncoupled from the introducer sheath and withdrawn from the patient. Other medical devices may then be inserted into the patient through the introducer sheath. The introducer sheath assemblies described herein may also be used in connection with other medical procedures, such as biopsy procedures, etc.

Figure 1A:
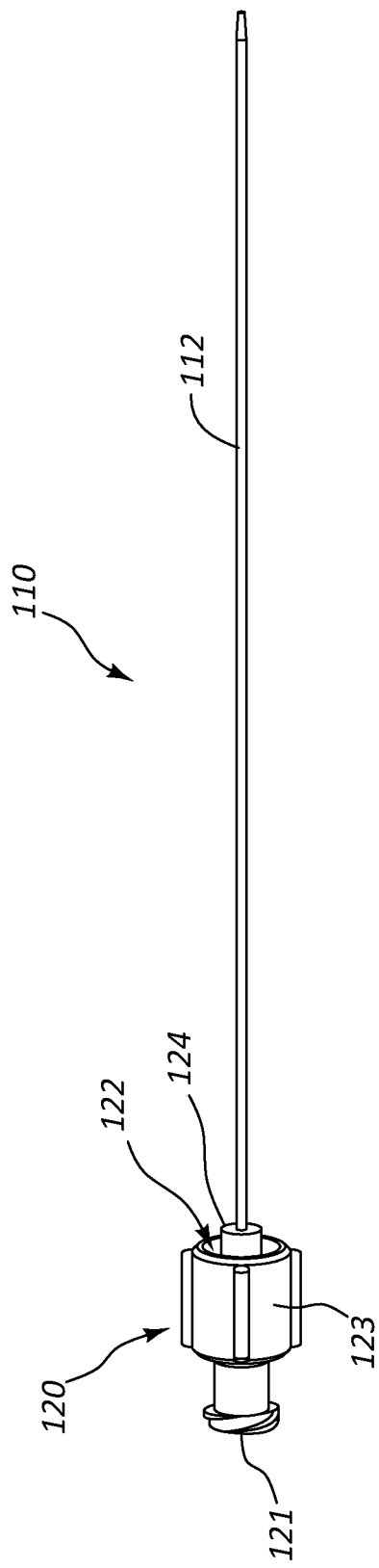
FIG. 1A is a side view of a dilator.
Figure 1B:
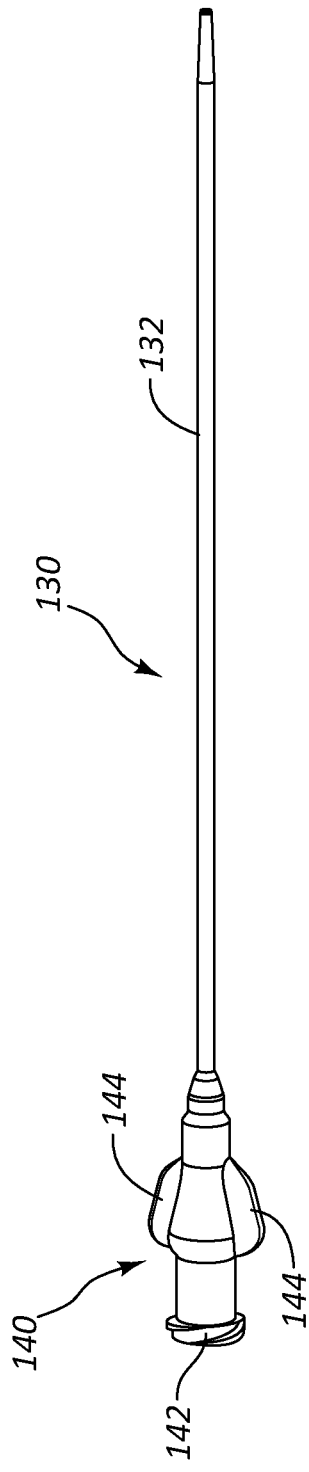
FIG. 1B is a side view of an introducer sheath.
Figure 1C:
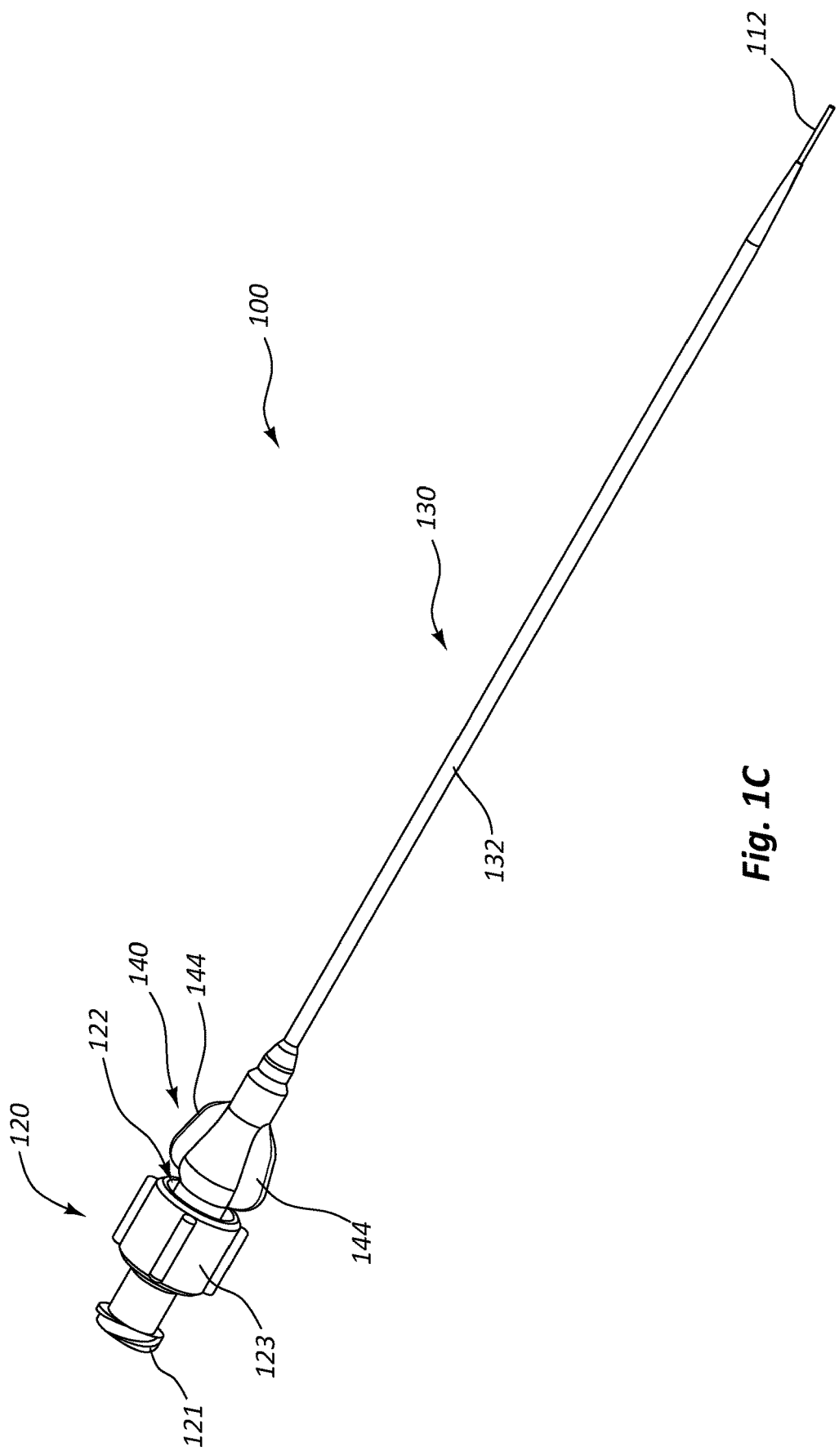
FIG. 1C is a perspective view of an introducer sheath assembly that includes the dilator of FIG. 1A and the introducer sheath of FIG. 1B.

FIGS. 1A-1C depict an introducer sheath assembly 100, or components thereof. In particular, FIG. 1A provides a side view of a dilator 110. FIG. 1B provides a side view of an introducer sheath 130. And FIG. 1C provides a perspective view of an introducer sheath assembly 100 in which the dilator 110 of FIG. 1A is coupled to the introducer sheath 130 of FIG. 1B.

With reference to FIG. 1A, the dilator 110 may include an elongate shaft 112 and a dilator hub 120 that is coupled to the elongate shaft 112 adjacent a proximal end of the elongate shaft 112. In the depicted embodiment, the dilator hub 120 includes a female luer lock fitting 121 adjacent the proximal end of the dilator hub 120, and a male luer lock fitting 122 that is disposed distal of the female luer lock fitting 121. The male luer lock fitting 122 includes a sleeve 123 having a plurality of threads (not shown) on its inner surface and a protuberance 124 that is at least partially disposed within the sleeve 123. The elongate shaft 112 may extend distally from the protuberance 124. The length of the elongate shaft 112 may approximate the length of an introducer sheath 130 to be used with the dilator 110. In some embodiments, the elongate shaft 112 partially defines a lumen (not shown) that extends through the dilator 110. Stated differently, in some embodiments, the elongate shaft 112 is a tube having a hollow interior.

With reference to FIG. 1B, the introducer sheath 130 may include an elongate tubular member 132 and an introducer sheath hub 140. In the depicted embodiment, the tubular member 132 is coupled to and extends distally from the introducer sheath hub 140. The tubular member 132 may partially define a lumen (not shown) that extends through the introducer sheath 130.

With reference to the embodiment depicted in FIGS. 1A-1C, the introducer sheath hub 140 may comprise a female luer lock fitting 142 and wings 144. In the depicted embodiment, the female luer lock fitting 142 is configured to facilitate coupling of the introducer sheath hub 140 to the dilator hub 120. Stated differently, the female luer lock fitting 142 is configured to threadably engage with the male luer lock fitting 122 of the dilator hub 120. Each of the wings 144 extends radially away from a longitudinal axis of the of the introducer sheath hub 140 and is configured to facilitate manipulation of the introducer sheath 130 by providing a gripping point for the practitioner.

The dilator 110 may be inserted within and coupled to the introducer sheath 130 to stiffen the introducer sheath 130 and/or ensure that the dilator 110 and the introducer sheath 130 travel as a single unit when advanced within a patient. For example, the elongate shaft 112 may be inserted through an opening adjacent the proximal end of the introducer sheath 130 and advanced within the introducer sheath 130 until the dilator hub 120 is adjacent to the introducer sheath hub 140. The dilator hub 120 may then be coupled to the introducer sheath hub 140 by rotating the dilator hub 120 relative to the introducer sheath hub 140, thereby securing the dilator hub 120 to the introducer sheath hub 140 via a luer lock engagement. Stated differently, when the dilator hub 120 is rotated relative to the introducer sheath hub 140, the threads of the female luer lock fitting 142 for the introducer sheath hub 140 may engage with threads on the sleeve 123 of the male luer lock fitting 122 of the dilator 110, thereby securing the dilator hub 120 to the introducer sheath hub 140. In some embodiments, an introducer sheath assembly 100 is packaged and/or delivered to the practitioner in an assembled configuration in which the dilator 110 is coupled to the introducer sheath 130. In other embodiments, the practitioner couples the dilator 110 to the introducer sheath 130.

Once the dilator 110 is coupled to the introducer sheath 130, a distal portion of the introducer sheath assembly 100 may be percutaneously inserted into and advanced within the patient. Once the introducer sheath 130 is properly placed within the patient, the dilator 110 may be uncoupled from the introducer sheath 130 by rotating the dilator 110 relative to the introducer sheath 130, thereby disconnecting the luer lock connection between the dilator 110 and the introducer sheath 130. Rotation of the dilator 110 relative to the introducer sheath 130 to uncouple the dilator 110 from the introducer sheath 130 generally requires two hands: one hand to grasp and rotate the dilator hub 120 and a second hand to grasp the introducer sheath hub 140 to prevent rotation of the introducer sheath 130 while the dilator hub 120 is rotated. The rotational force that is applied to uncouple the dilator 110 from the introducer sheath 130 may affect the positioning of the introducer sheath 130 within the patient. For example, in some instances, the distal end of the introducer sheath 130 may be inadvertently displaced as the practitioner attempts to rotate the dilator hub 120 relative to the introducer sheath hub 140.

FIGS. 2A-2D depict an embodiment of an introducer sheath assembly 200 that resembles the introducer sheath assembly 100 described above in certain respects. Accordingly, like features are designated with like reference numerals, with the leading digits incremented to "2." For example, the embodiment depicted in FIGS. 2A-2D includes a dilator 210 that may, in some respects, resemble the dilator 110 of FIGS. 1A-1C. Relevant disclosure set forth above regarding similarly identified features thus may not be repeated hereafter. Moreover, specific features of introducer sheath assemblies and related components shown in FIGS. 1A-1C may not be shown or identified by a reference numeral in the drawings or specifically discussed in the written description that follows. However, such features may clearly be the same, or substantially the same, as features depicted in other embodiments and/or described with respect to such embodiments. Accordingly, the relevant descriptions of such features apply equally to the features of the introducer sheath assembly 200 and related components depicted in FIGS. 2A-2D. Any suitable combination of the features, and variations of the same, described with respect to the introducer sheath assembly 100 and related components illustrated in FIGS. 1A-1C can be employed with the introducer sheath assembly 200 and related components of FIGS. 2A-2D, and vice versa. This pattern of disclosure applies equally to further embodiments depicted in subsequent figures and described hereafter, wherein the leading digits may be further incremented.

Figure 2A:
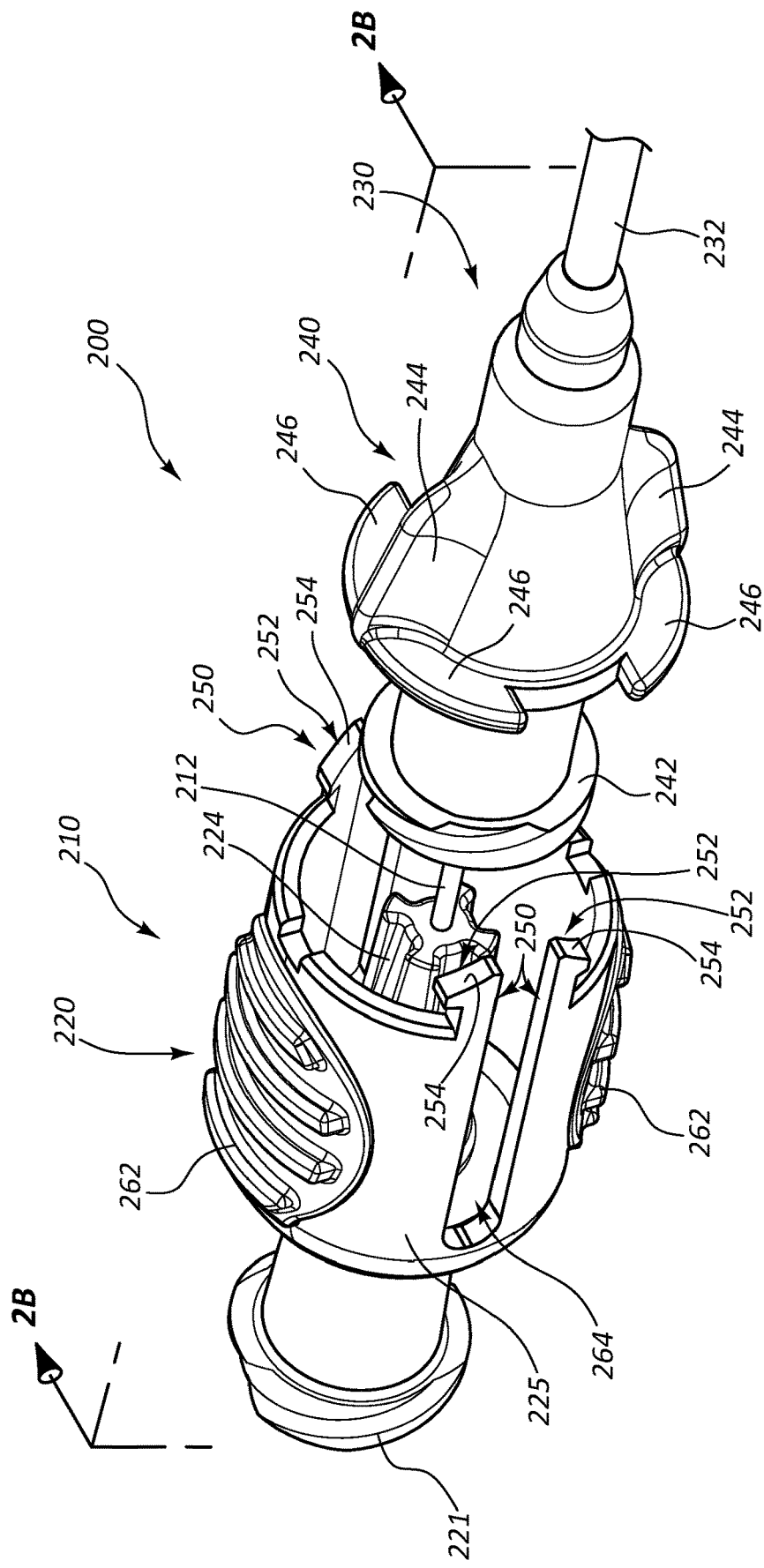
FIG. 2A is a perspective view of an unassembled introducer sheath hub assembly according to another embodiment.
Figure 2B:
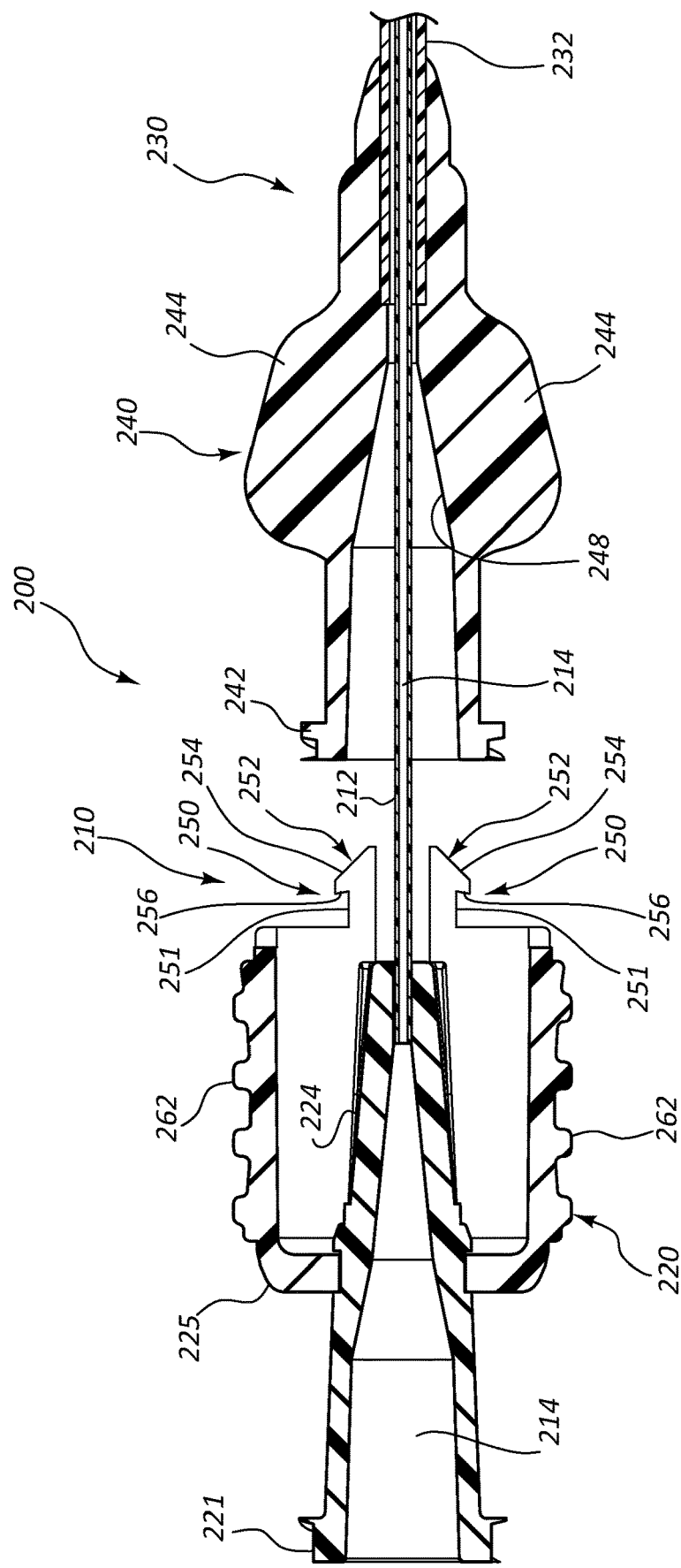
FIG. 2B is a cross-sectional side view of the unassembled introducer sheath hub assembly of FIG. 2A.
Figure 2C:
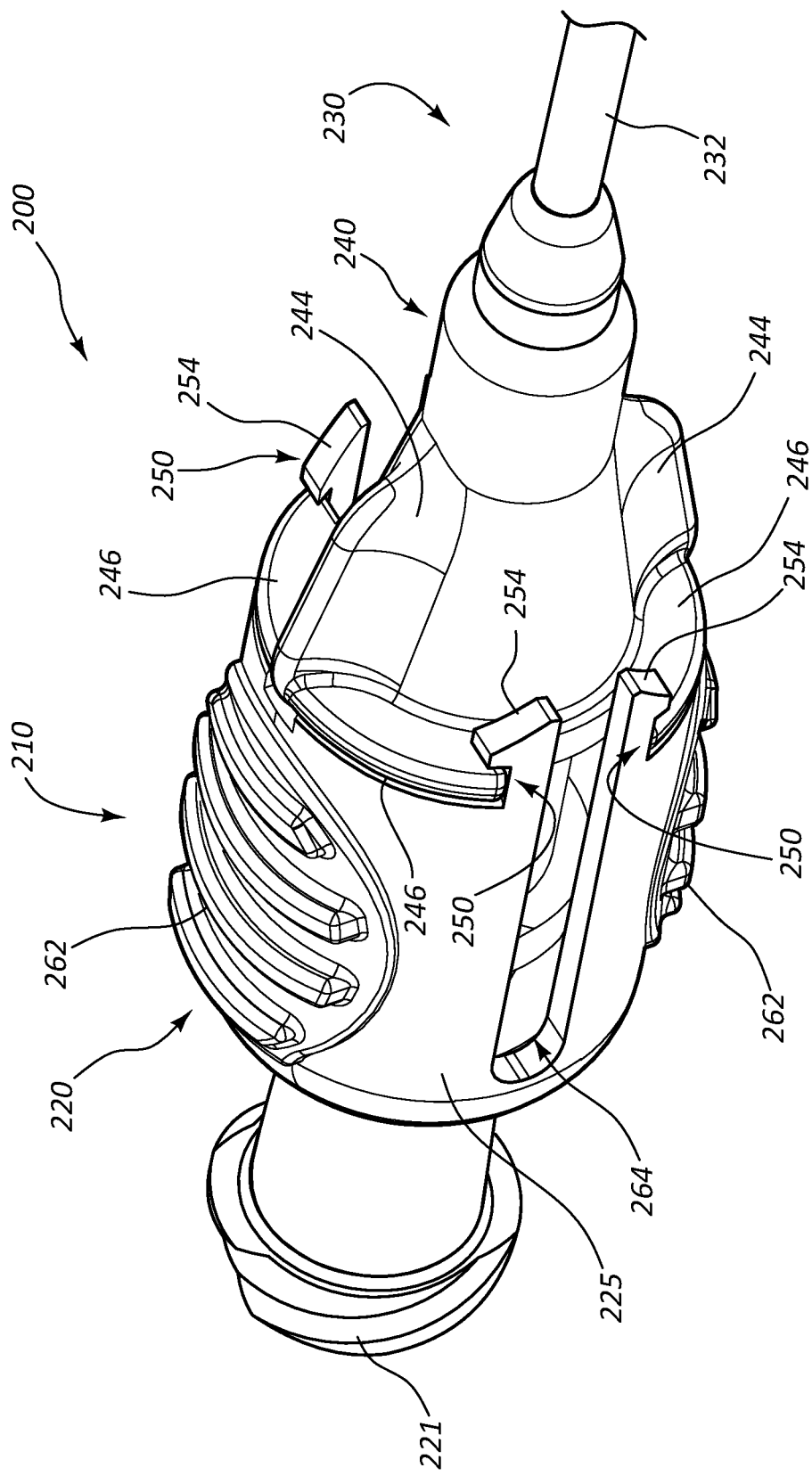
FIG. 2C is a perspective view of the introducer sheath hub assembly of FIGS. 2A and 2B in an assembled configuration.
Figure 2D:
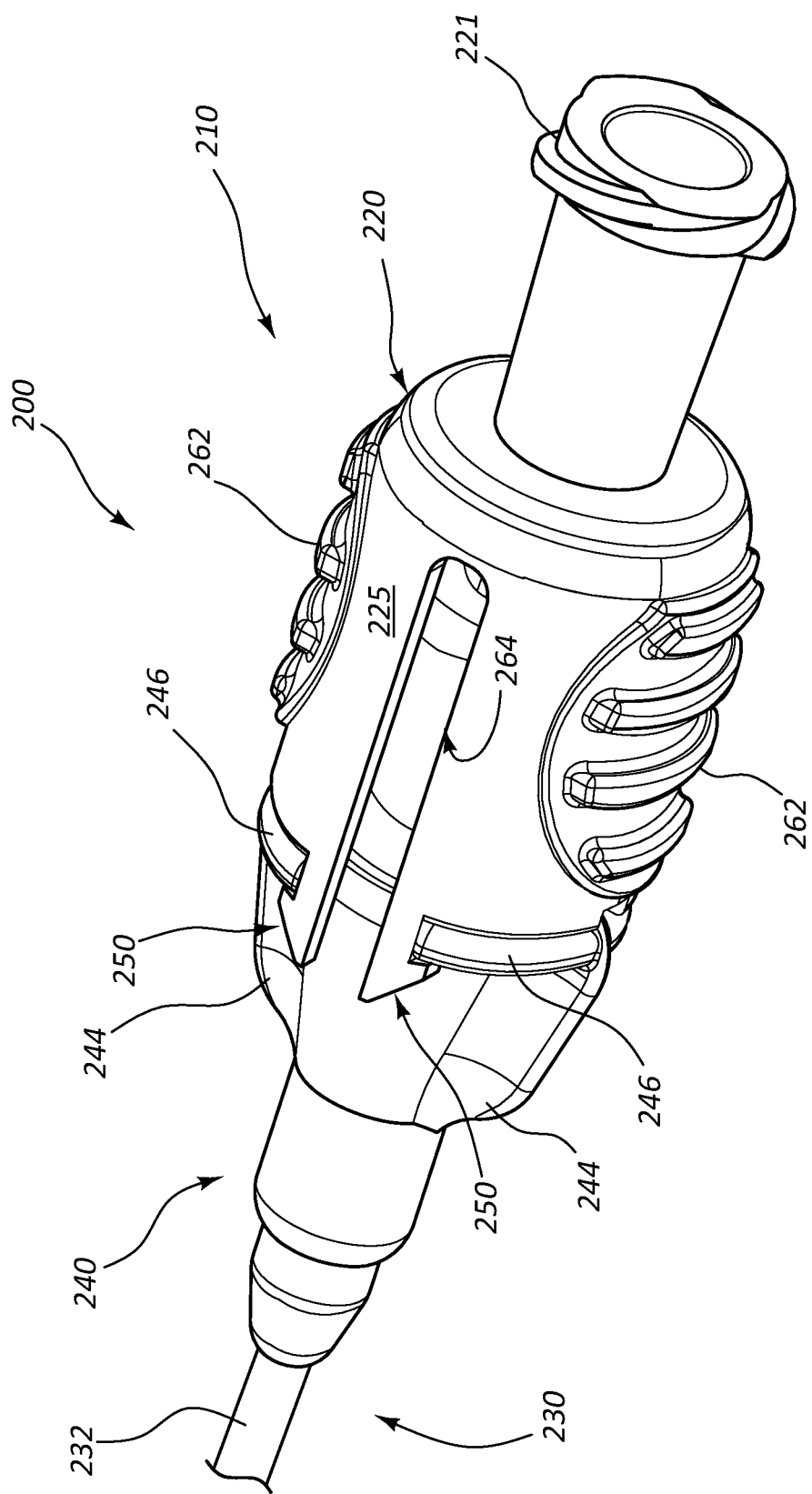
FIG. 2D is another perspective view of the introducer sheath hub assembly of FIGS. 2A-2C in an assembled configuration.

FIGS. 2A-2D provide various views of an introducer sheath assembly 200 and related components. More particularly, FIG. 2A provides a perspective view of the introducer sheath assembly 200 in an unassembled configuration. FIG. 2B provides a cross-sectional side view of the unassembled introducer sheath assembly 200. And FIGS. 2C and 2D provide alternative perspective views of the introducer sheath assembly 200 in an assembled configuration. In the depicted embodiment, the introducer sheath assembly 200 is substantially symmetrical across two planes: (1) the plane used to define the cross-section depicted in FIG. 2B, and (2) the plane going into the page of FIG. 2B that bisects the introducer sheath assembly 200 along the longitudinal axis of the introducer sheath assembly 200.

With reference to FIGS. 2A-2D, the introducer sheath assembly 200 may include a dilator 210 and an introducer sheath 230. The dilator 210 may include an elongate shaft 212 and a dilator hub 220. The elongate shaft 212 may comprise a tubular member that defines, in part, a lumen 214 that extends through the dilator 210. The lumen 214 may be sized to accommodate a guidewire (not shown). In the depicted embodiment, the dilator hub 220 includes a female luer lock fitting 221, a protuberance 224, a cylindrical member 225, finger input portions 262, and catches 250.

In the depicted embodiment, the protuberance 224 is at least partially disposed within the cylindrical member 225. In some embodiments, the protuberance 244 is configured to contact an inner surface 248 of the introducer sheath hub 240 when the dilator 210 is coupled to the introducer sheath 230. The elongate shaft 212 may extend distally from the protuberance 224. In the depicted embodiment, the elongate shaft 212 is a hollow tube. Stated differently, the elongate shaft 212 may include a tubular member that at least partially defines a lumen 214 that extends through the elongate shaft 212.

In the depicted embodiment, cylindrical member 225 includes two finger input portions 262 and two slits 264. The two finger input portions 262 are positioned on opposite sides of the dilator hub 220. The two slits 264 are also positioned on opposite sides of the dilator hub 220 and are radially offset from the finger input portions 262 relative to a longitudinal axis of the dilator hub 220. As described in further detail below, the finger input portions 262 are configured to facilitate uncoupling of the dilator hub 220 from the introducer sheath hub 240 when pressed toward one another.

In the depicted embodiment, the catches 250 extend distally from a proximal portion of the dilator hub 220. Each catch 250 may include a tail 251 and a barb 252. As depicted in FIGS. 2A-2D, the barb 252 may include a leading angled surface 254 and a trailing surface 256. The catches 250 may be radially offset from the finger input portions 262.

The introducer sheath 230 may include a tubular member 232 and an introducer sheath hub 240. The tubular member 232 may partially define a lumen (not shown) that extends through the introducer sheath 230. The introducer sheath hub 240 may include a female luer lock fitting 242, wings 244, and two or more semi-annular ridges 246. In contrast with the embodiment depicted in FIGS. 1A and 1C, the female luer lock fitting 242 does not threadably engage with the dilator hub 220, as the dilator hub 220 does not include threads for mating with the female luer lock fitting 242.

The wings 244 may include a first wing and a second wing that each extend radially away from the longitudinal axis of the introducer sheath hub 240. Stated differently, the wings 244 may each extend radially away from a longitudinal axis of the introducer sheath hub 240.

The two or more semi-annular ridges 246 may protrude radially away from a longitudinal axis of the introducer sheath hub 240. In the depicted embodiments, each semi-annular ridge 246 extends less than halfway around the circumference of the introducer sheath hub 240. The semi-annular ridges 246 may be spaced from one another to provide for openings between the semi-annular ridges 246. As described in further detail below, these ridges 246 may be configured to interact with the catches 250 to couple the dilator hub 220 to the introducer sheath hub 240.

The dilator 210 may be inserted within and coupled to introducer sheath 230. For example, the distal end of the dilator 210 may be inserted through a proximal opening of the introducer sheath 230 and advanced within the introducer sheath 230. As the dilator 210 is advanced within the introducer sheath 230, each catch 250 may approach a semi-annular ridge 246. More particularly, as the dilator 210 is advanced within the introducer sheath 230, the leading angled surface 254 of each barb 252 may interact with a ridge 246, thereby causing displacement and/or deflection of the catch 250. Such displacement and/or deflection may narrow the width of a distal portion of the slit 264. As the catches 250 are displaced and/or deflected, each catch 250 may at least partially pass through an opening between the ridges 246. Stated differently, displacement and/or deflection of the catches 250 may allow the barbs 252 to extend past the ridges 246. Once the barbs 252 of the catches 250 have passed through the openings, the catches 250 may engage with the ridges 246 to couple the dilator hub 220 to the introducer sheath hub 240. Stated differently, when the dilator hub 220 is coupled to the introducer sheath hub 240, the barbs 252 may be disposed distal of the ridges 246 and impede withdrawal of the dilator 210 from the introducer sheath 230 due to the impediment provided by the trailing surfaces 256 of the barbs 252.

As the introducer sheath assembly 200 transitions from a configuration in which the dilator hub 220 is uncoupled from the introducer sheath hub 240 to a configuration in which the dilator hub 220 is coupled to the introducer sheath hub 240, the catches 250 may snap in place, thereby providing audible and/or tactile feedback to the practitioner. Once the dilator hub 220 is coupled to the introducer sheath hub 240, the practitioner may visually inspect the coupling and confirm that the catches 250 are properly engaged with the ridges 246. Stated differently, the introducer sheath assembly 200 may include a positive stop that is visually observable when the dilator hub 220 is coupled to the introducer sheath hub 240.

In some embodiments, the process of inserting the dilator 210 into the introducer sheath 230 and coupling the dilator 210 to the introducer sheath 230 may be accomplished (1) without rotating the dilator hub 220 relative to the introducer sheath hub 240, (2) without applying an external force directly to the finger input portions 262 (e.g., without squeezing or pressing the finger input portions 262 toward one another), and/or (3) by a mechanism that does not involve an interaction between threads on the dilator hub 220 and threads on the introducer sheath hub 240.

Once the dilator 210 has been coupled to the introducer sheath 230, a portion of the introducer sheath assembly 200 may be percutaneously inserted into a patient to facilitate the introduction of a medical device into the vasculature of a patient. For example, in an illustrative procedure, a needle may be used to create an initial access puncture into the patient's vasculature. A guidewire may then be threaded through the needle. Once the guidewire has been properly placed, the needle used to access the patient's vasculature may be withdrawn from the patient. The introducer sheath assembly 200 may then be threaded over the guidewire that has been placed within the patient. More specifically, the proximal end of the guidewire may be inserted into the distal end of the lumen 214 while the dilator 210 is coupled to the introducer sheath 230. The guidewire may be threaded through the lumen 214 until the proximal end of the guidewire emerges from the proximal end of the dilator 210. The introducer sheath assembly 200 may then be advanced over the guidewire to insert a distal region of the introducer sheath assembly 200 into the patient. Stated differently, the introducer sheath 230 and dilator 210 may be inserted into and advanced within the patient while the dilator 210 is disposed within the introducer sheath 230. The dilator 210 may impart increased stiffness to the introducer sheath 230, thereby facilitating insertion of the introducer sheath assembly 200 into the patient.

Once the introducer sheath 230 has been properly positioned within the patient, the dilator 210 may be uncoupled from the introducer sheath 230 and withdrawn from the introducer sheath 230. For example, the dilator hub 220 may be uncoupled from the introducer sheath hub 240 by first pressing the finger input portions 262 toward one another (i.e., squeezing the finger input portions 262). Pressing the finger input portions 262 toward one another may cause each catch 250 to deflect away from a semi-annular ridge 246, thereby narrowing the width of a distal portion of the slit 264. Once the catches 250 have been deflected away from the semi-annular ridges 246, the dilator 210 may be withdrawn from the introducer sheath 230. Stated differently, when the finger input portions 262 are pressed toward one another and thereby displace the catches 250, the barb 252 of each catch 250 may be displaced, thereby allowing each barb 252 to be retracted through an opening between the ridges 246.

In some embodiments, the process of uncoupling the dilator hub 220 from the introducer sheath hub 240 may be accomplished without rotating the dilator hub 220 relative to the introducer sheath hub 240. In other or further embodiments, the process of uncoupling the dilator hub 220 from the introducer sheath hub 240 may be accomplished using only a single hand. Additionally or alternatively, the dilator hub 220 may be uncoupled from the introducer sheath hub 240 via a mechanism that does not involve an interaction between threads on the dilator hub 220 and threads on the introducer sheath hub 240.

Figure 3A:
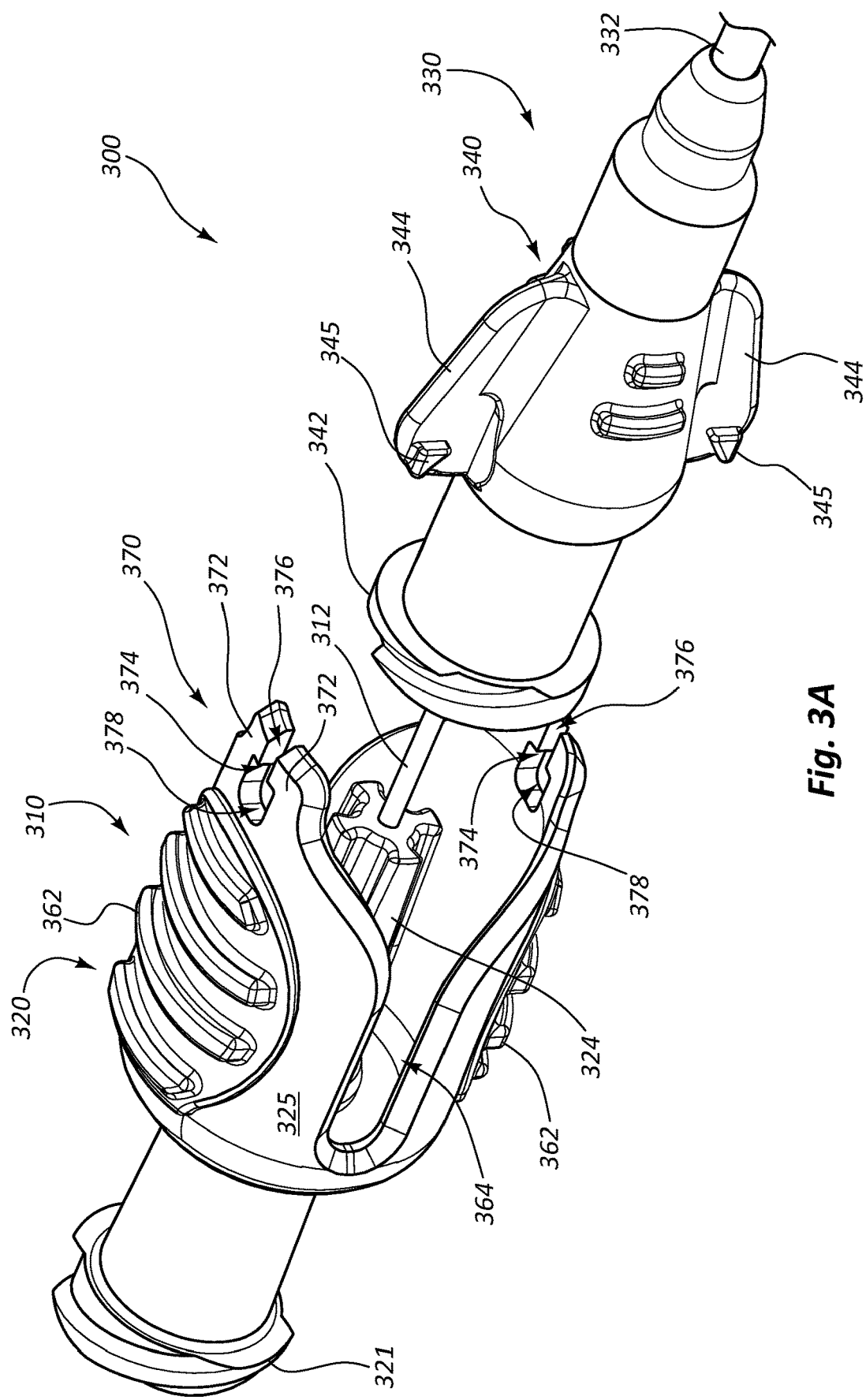
FIG. 3A is a perspective view of an unassembled introducer sheath hub assembly according to another embodiment.
Figure 3B:
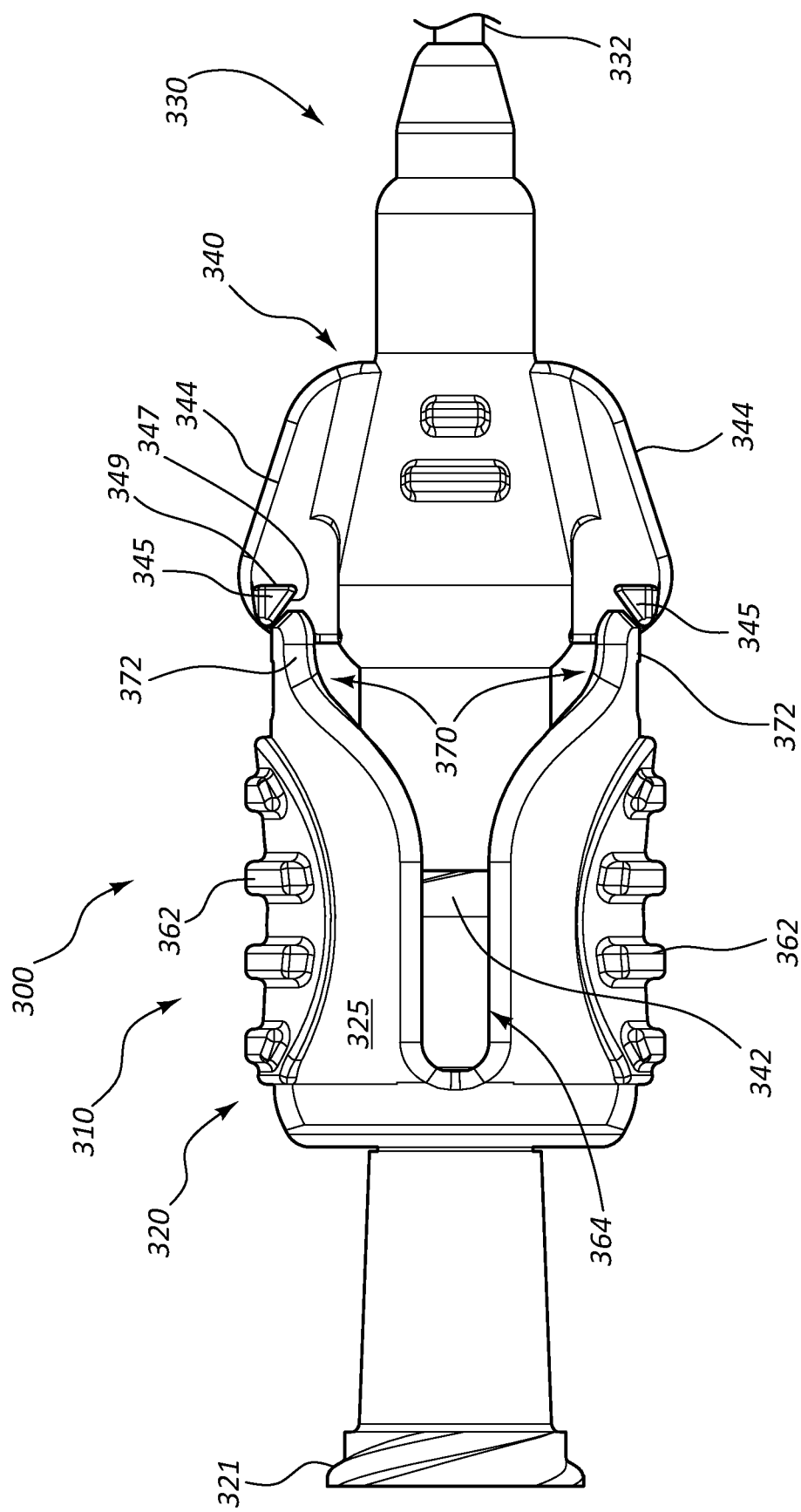
FIG. 3B is a side view of the introducer sheath hub assembly of FIG. 3A in another unassembled configuration.
Figure 3C:
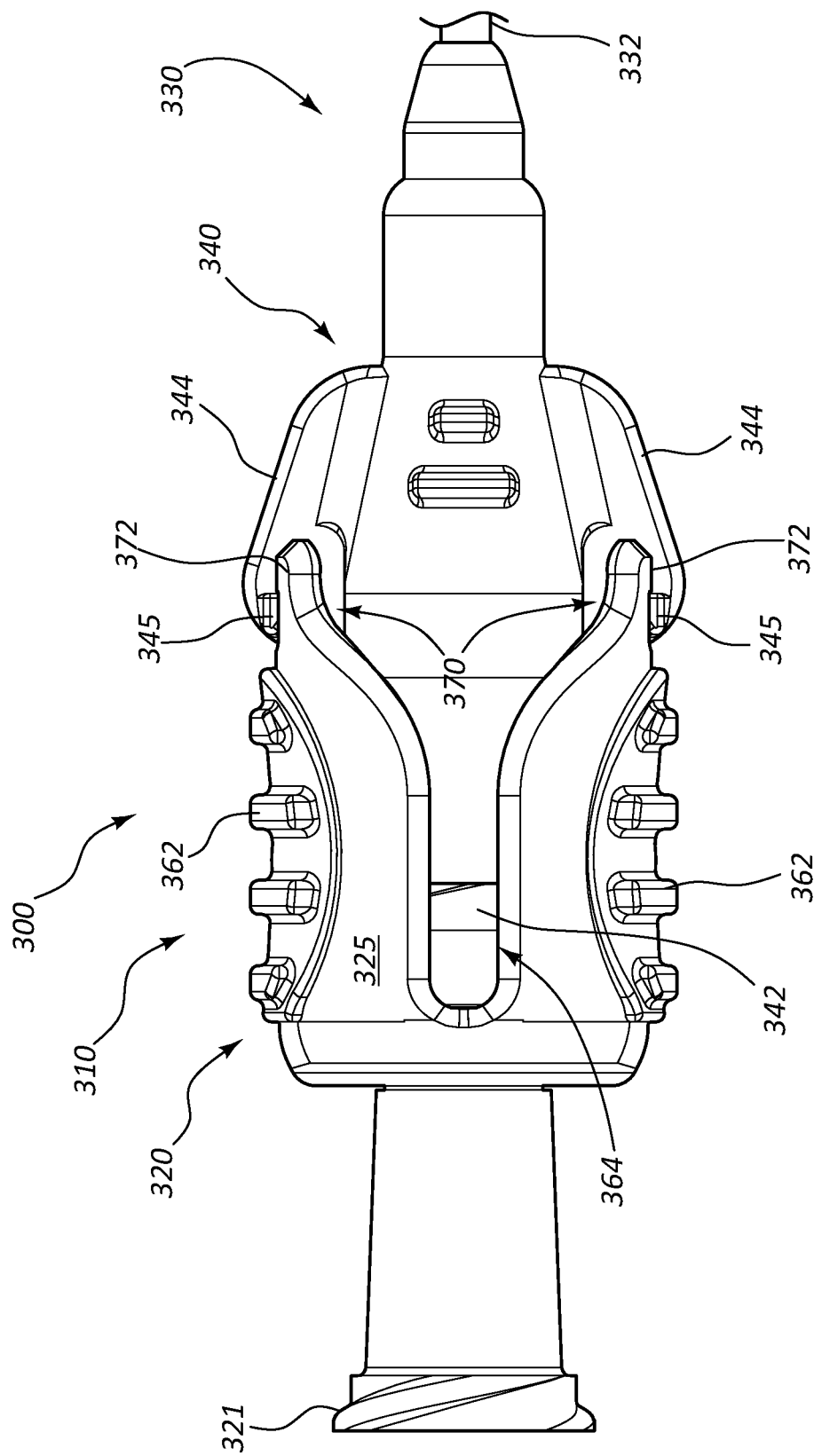
FIG. 3C is a side view of the introducer sheath hub assembly of FIGS. 3A and 3B in an assembled configuration.
Figure 3D:
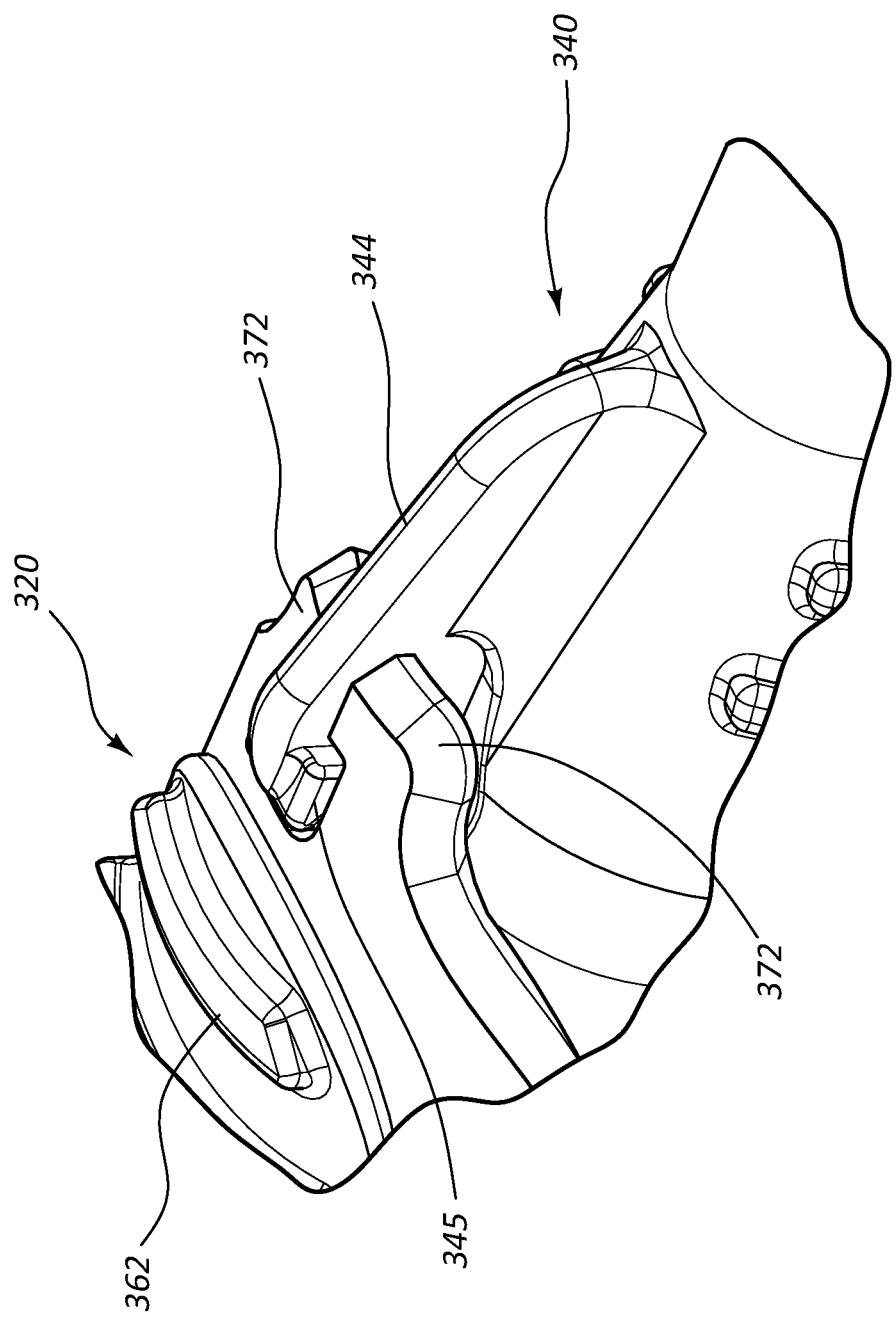
FIG. 3D is a close-up perspective view of a portion of the introducer sheath hub assembly of FIGS. 3A and 3B in an assembled configuration.

FIGS. 3A-3D depict an introducer sheath assembly 300 according to another embodiment. More particularly, FIG. 3A provides a perspective view of the introducer sheath assembly 300 in an unassembled state. FIG. 3B provides a side view of the introducer sheath assembly 300 in another unassembled state. FIG. 3C provides a side view of the introducer sheath assembly 300 in an assembled state. And FIG. 3D provides a perspective view of the introducer sheath assembly 300 in an assembled state. In the depicted embodiment, the introducer sheath assembly 300 is substantially symmetrical across two planes: (1) the "vertical" plane that both bisects the wings 344 and extends through the finger input portions 362 and (2) the "horizontal" plane that bisects the slits 364.

With reference to FIGS. 3A-3D, the introducer sheath assembly 300 may include a dilator 310 and an introducer sheath 330. The dilator 310 may include an elongate shaft 312 and a dilator hub 320. The elongate shaft 312 may include a tubular member that defines, in part, a lumen (not shown) that extends through the dilator 310. In the depicted embodiment, the dilator hub 320 includes a female luer lock fitting 321, a protuberance 324, a cylindrical member 325, finger input portions 362, and coupling regions 370 that are each radially aligned with a finger input portion 362. The female luer lock fitting 321, the protuberance 324, the cylindrical member 325, and finger input portions 362 are generally analogous to similar features identified in connection with the introducer sheath assembly 200.

In the embodiment depicted in FIGS. 3A-3D, the coupling region 370 of the dilator hub 320 extends distally from a proximal region of the dilator hub 320. The coupling region 370 may include two hooks 372 that form a gap 374 disposed between the two hooks 372. The gap 374 may include a distal portion 376 and a proximal portion 378. In some embodiments, the distal portion 376 of the gap 374 is narrower than the proximal portion 378 of the gap 374.

The introducer sheath 330 may include a tubular member 332 and an introducer sheath hub 340. The tubular member 332 may partially define a lumen (not shown) that extends through the introducer sheath 330. The introducer sheath hub 340 may include a female luer lock fitting 342, wings 344, and protrusions 345. In the depicted embodiment, the female luer lock fitting 342 does not threadably engage with the dilator hub 320, as the dilator hub 320 does not include threads for mating with the female luer lock fitting 342.

The wings 344 may include a first wing and a second wing that each extend radially away from the longitudinal axis of the introducer sheath hub 340. In the depicted embodiment, each wing 344 includes two protrusions 345 that extend in opposite directions from the wing 344. Stated differently, for each wing 344, a first protrusion 345 may extend from a first side of the wing 344 and a second protrusion 345 may extend from a second side of the wing 344.

The protrusions 345 may be shaped in any suitable manner. For example, in the embodiment depicted in FIGS. 3A-3D, the protrusions 345 are shaped as triangular prisms. In the depicted embodiment, each protrusion 345 includes an angled surface 347 and a distal surface 349. The angled surface 347 may extend distally toward the longitudinal axis of the introducer sheath hub 340. Stated differently, the angled surface 347 may be slanted such that a distal portion of the angled surface 347 is disposed closer to the longitudinal axis of the introducer sheath hub 340 than a proximal portion of the angled surface 347. In contrast with the introducer sheath hub 240 described above in connection with FIGS. 2A-2D, the introducer sheath hub 340 does not include semi-annular ridges that are configured for coupling to a barbed catch. The omission of such semi-annular ridges may allow the introducer sheath hub 340 to have a lower profile than the introducer sheath hub 240.

The dilator 310 may be inserted within and coupled to introducer sheath 330. For example, the distal end of the dilator 310 may be inserted through a proximal opening of the introducer sheath 330 and advanced within the introducer sheath 330. As the dilator 310 is advanced within the introducer sheath 330, the coupling regions 370 may approach the protrusions 345 as shown in FIG. 3B. More particularly, as the dilator 310 is advanced within the introducer sheath 330, the distal ends of the hooks 372 may interact with the angled surfaces 347 of the protrusions 345, thereby causing displacement and/or deflection of the coupling regions 370 toward the longitudinal axis of the dilator 310. Such displacement and/or deflection may narrow the width of a distal portion of the slits 364 that extend along a portion of the dilator hub 320 and are radially offset from the finger input portions 262. As the coupling regions 370 are displaced and/or deflected, the hooks 372 may be forced toward the longitudinal axis of the dilator 310 due to interaction with the angled surfaces 347, thereby allowing a distal portion of each hook 372 to extend past the protrusion 345. Once the distal portion of the hook 372 is disposed distal of the protrusion 345, the distal portion of the hook 372 may engage with the distal surface 349 of the protrusion 345 to couple the dilator hub 320 to the introducer sheath hub 240. Stated differently, when the dilator hub 320 is coupled to the introducer sheath hub 340, a distal portion of the coupling region 370 (e.g., distal portions of the hooks 372) may be disposed distal of the protrusions 345 and impede withdrawal of the dilator 310 from the introducer sheath 330 due to the interaction between the hooks 372 and the distal surfaces 349 of the protrusions 345.

In some instances, as the introducer sheath assembly 300 transitions from a configuration in which the dilator hub 320 is uncoupled from the introducer sheath hub 340 to a configuration in which the dilator hub 320 is coupled to the introducer sheath hub 340, the coupling regions 370 may snap in place once the distal ends of the hooks 372 have cleared the protrusions 345, thereby providing audible and tactile feedback to the practitioner (or to anyone else who couples the dilator 310 to the introducer sheath 330). Once dilator hub 320 is coupled to the introducer sheath hub 340, the practitioner may visually inspect the coupling and confirm that the coupling hooks 372 are properly engaged with the protrusions 345. Stated differently, the introducer sheath assembly 300 may include a positive stop that is visually observable when the dilator hub 320 is coupled to the introducer sheath hub 340.

In some embodiments, the process of inserting the dilator 310 into the introducer sheath 330 and coupling the dilator 310 to the introducer sheath 330 may be accomplished (1) without rotating the dilator hub 320 relative to the introducer sheath hub 340, (2) without applying an external force directly to the finger input portions 362 (e.g., without squeezing or pressing the finger input portions 362 toward one another), and/or (3) by a mechanism that does not involve an interaction between threads on the dilator hub 320 and threads on the introducer sheath hub 340.

Once the dilator 310 has been coupled to the introducer sheath 330, a portion of the introducer sheath assembly 300 may be percutaneously inserted into a patient in a manner analogous to that described above in connection with the introducer sheath assembly 200.

Once the introducer sheath 330 of the introducer sheath assembly 300 has been properly positioned within the patient, the dilator 310 may be uncoupled from the introducer sheath 330 and withdrawn from the introducer sheath 330. For example, the dilator hub 320 may be uncoupled from the introducer sheath hub 340 by first pressing the finger input portions 362 toward one another (i.e., squeezing the finger input portions 362). When the finger input portions are pressed toward one another, each coupling region 370 (including hooks 372) may be deflected toward the longitudinal axis of the dilator 310, thereby narrowing the width of a distal portion of the slit 364. Once the distal portions of the hooks 372 have been deflected toward the longitudinal axis of the dilator 310, the dilator 310 may be withdrawn from the introducer sheath 330.

In this manner, the dilator hub 320 may be single-handedly uncoupled from introducer sheath hub 340 without rotating the dilator hub 320 relative to the introducer sheath hub 340. Further, the dilator hub 320 and the introducer sheath hub 340 may be coupled and uncoupled from one another by a process that does not involve threads.

Figure 4A:
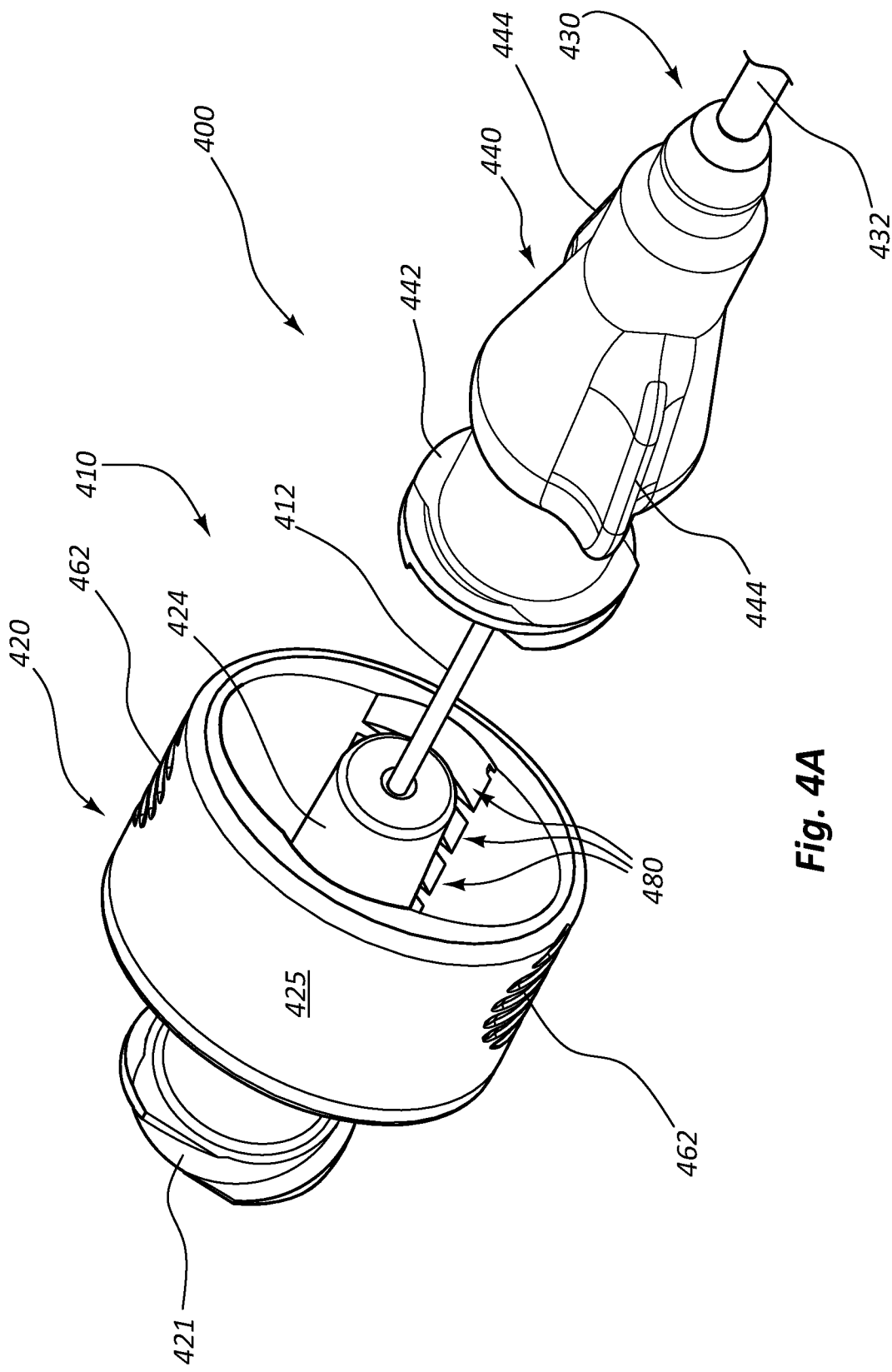
FIG. 4A is a perspective view of an unassembled introducer sheath hub assembly according to another embodiment.
Figure 4B:
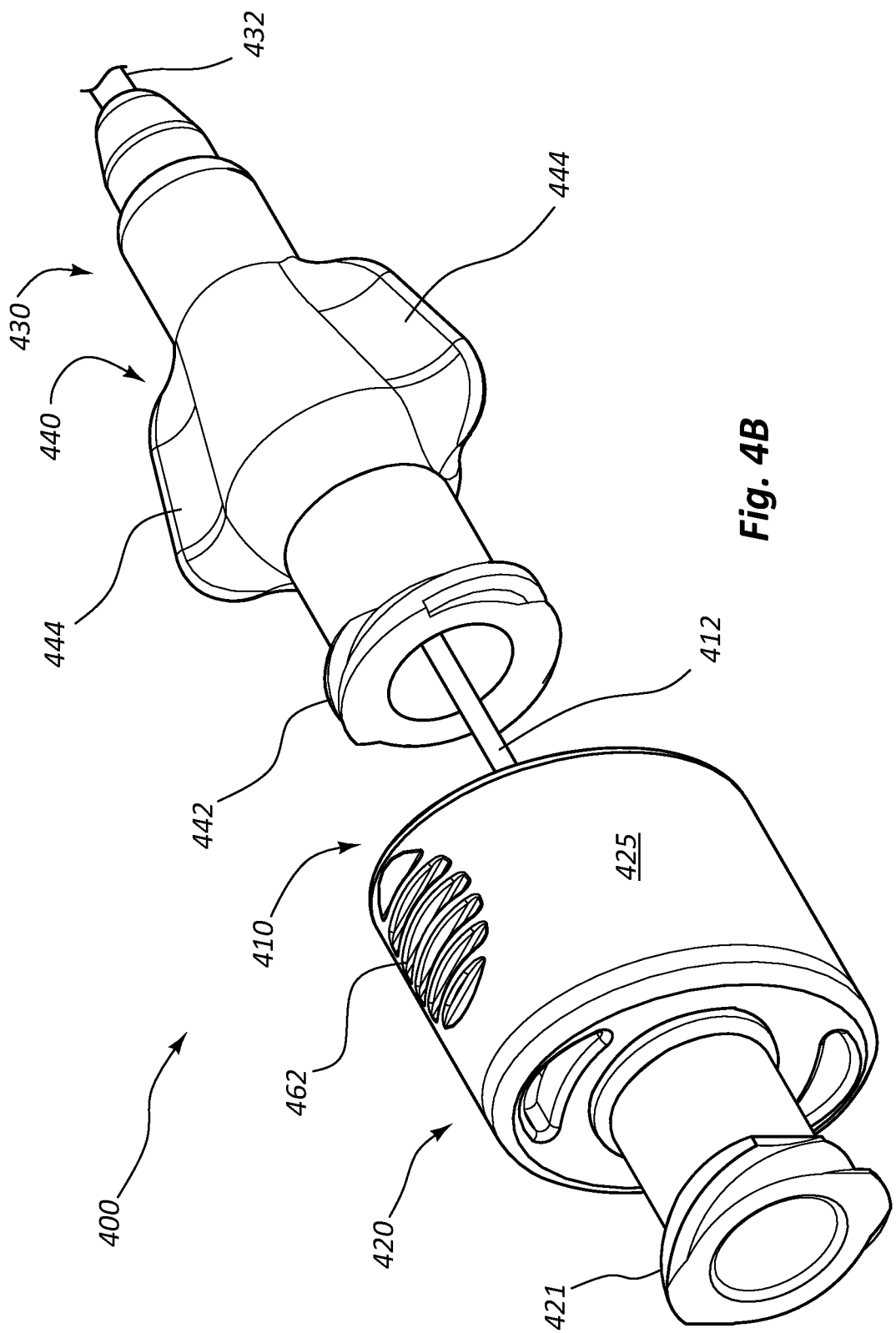
FIG. 4B is an alternative perspective view of the introducer sheath hub assembly of FIG. 4A.
Figure 4C:
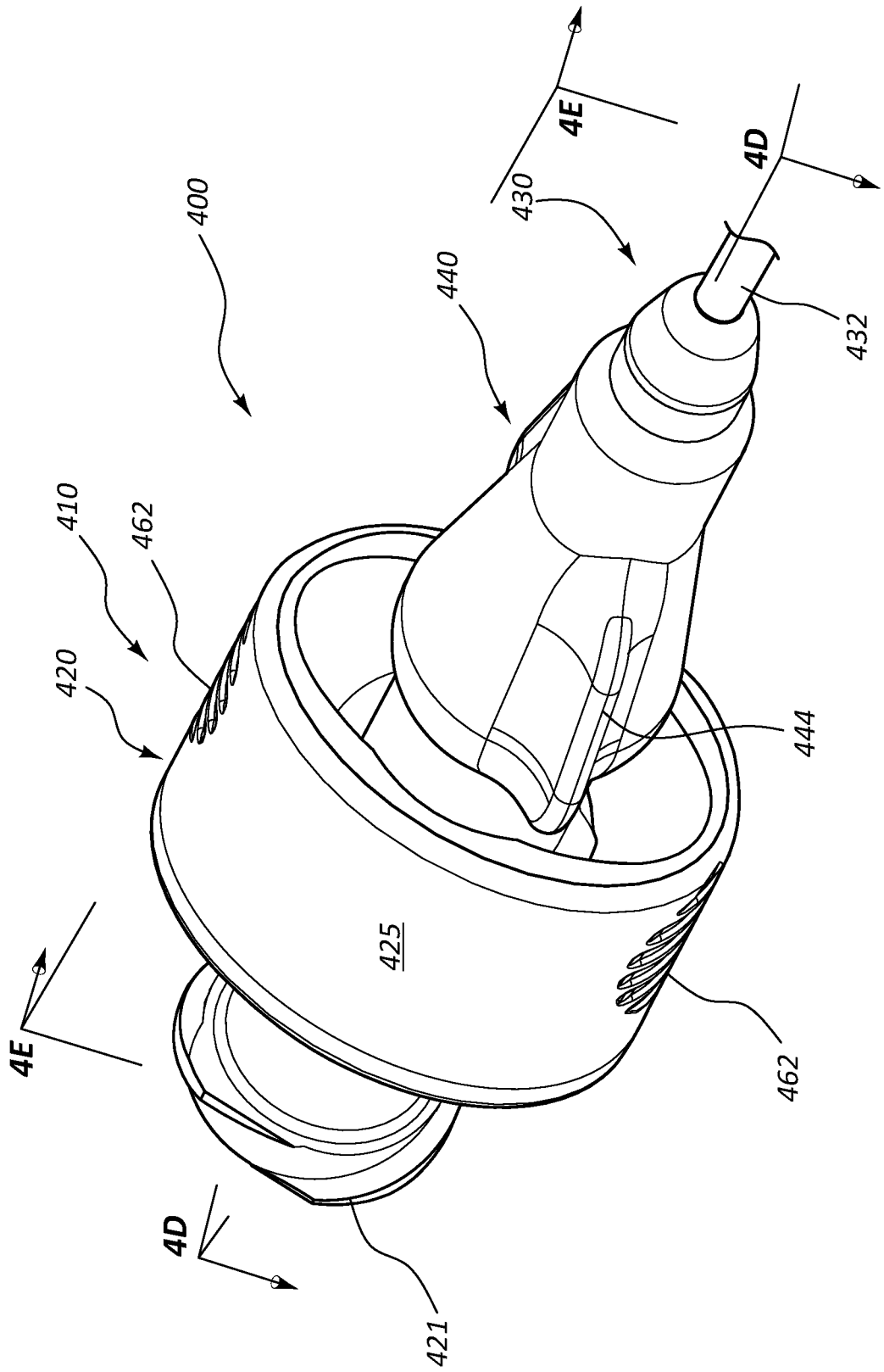
FIG. 4C is a perspective view of the introducer sheath hub assembly of FIG. 4A in an assembled configuration.
Figure 4G:
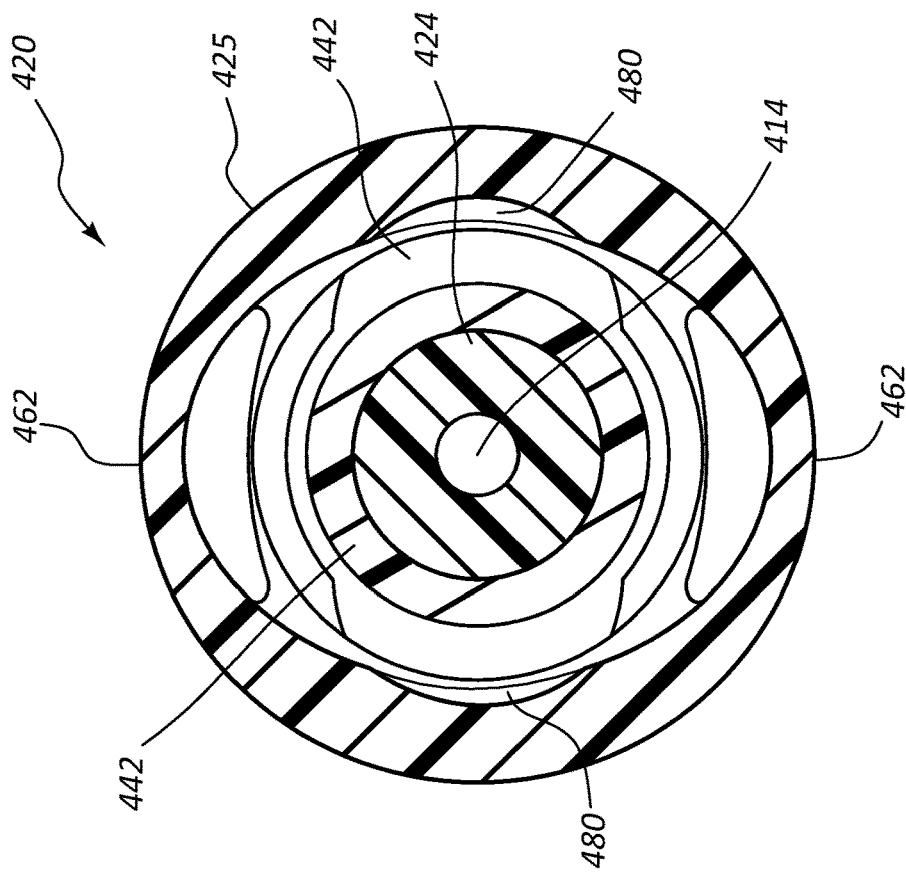
FIG. 4G is another cross-sectional view of the assembled introducer sheath hub assembly of FIG. 4A with a cylindrical member in a constrained configuration.
Figure 4F:
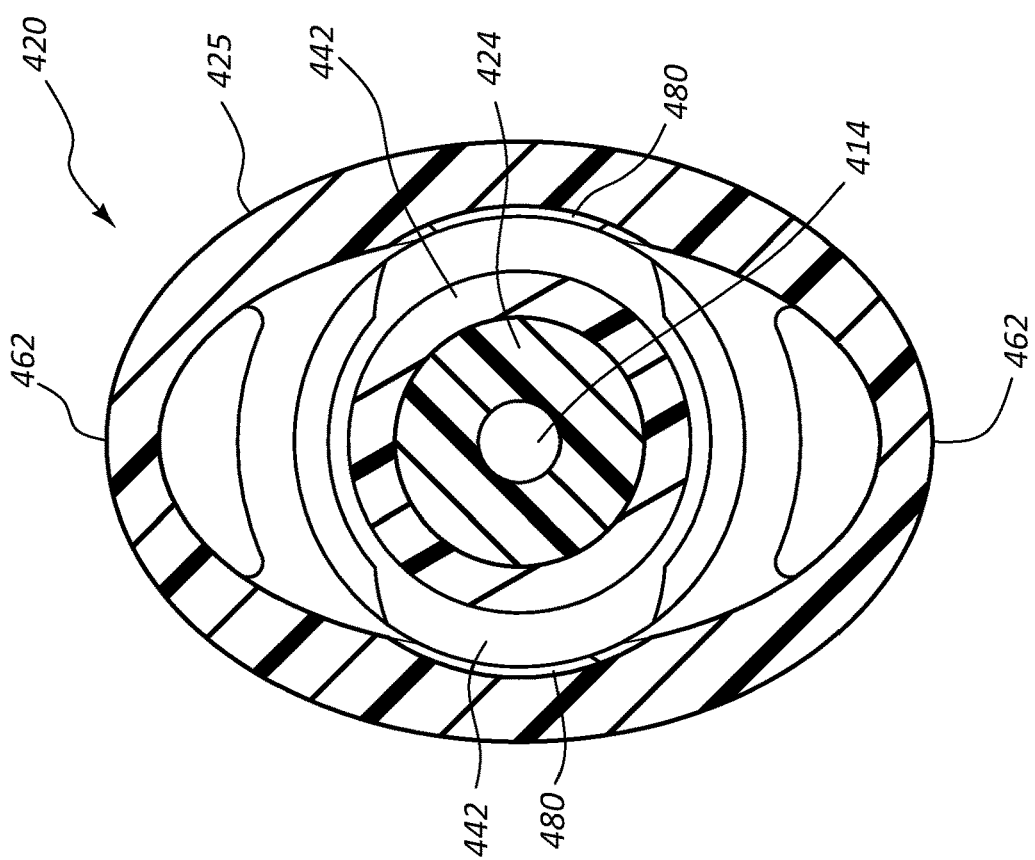
FIG. 4F is another cross-sectional view of the assembled introducer sheath hub assembly of FIG. 4A with a cylindrical member in an unconstrained configuration.

FIGS. 4A-4G depict an introducer sheath assembly 400 according to another embodiment. More particularly, FIGS. 4A and 4B provide alternative perspective views of the introducer sheath assembly 400 in an unassembled configuration. FIG. 4C provides a perspective view of the introducer sheath assembly 400 in an assembled configuration. FIGS. 4D and 4E provide alternative cross-sectional side views of the assembled introducer sheath assembly 400. And FIGS. 4F and 4G provide cross-sectional front views of the introducer sheath assembly 400 in an unconstrained (FIG. 4F) and constrained (FIG. 4G) configuration.

With reference to FIGS. 4A-4G, the introducer sheath assembly 400 may include a dilator 410 and an introducer sheath 430. The dilator 410 may include an elongate shaft 412 and a dilator hub 420. The elongate shaft 412 may include a tubular member that defines, in part, a lumen 414 that extends through the dilator 410. In the depicted embodiment, the dilator hub 420 includes a female luer lock fitting 421, a protuberance 424, a cylindrical member 425, and finger input portions 462. The female luer lock fitting 421, the protuberance 424, and the finger input portions 462 are generally analogous to similar features identified in connection with other introducer sheath assemblies described herein.

In the depicted embodiment, the base of the cylindrical member 425, when unconstrained, is oblong in shape. For example, in some embodiments the base of the cylindrical member 425, when unconstrained, is oval or elliptical in shape. Stated differently, a plane that is perpendicular to the longitudinal axis of the cylindrical member 425 may intersect the cylindrical member 425 to form an oblong shape when the cylindrical member 425 is in an unconstrained configuration.

In the depicted embodiment, the cylindrical member 425 includes one or more protrusions 480. In some embodiments, the one or more protrusions 480 are radially offset from the finger input portions 462. The one or more protrusions 480 may be disposed on and/or extend radially inward from an inner surface of the cylindrical member 425. The cylindrical member 425 may be made from resilient material, such as a resilient polyethylene, polypropylene, polyurethane, or another type of resilient material.

The introducer sheath 430 is generally analogous to the introducer sheath 130 depicted in FIG. 1B. As depicted in FIGS. 4A-4E, the introducer sheath 430 includes a tubular member 432 and an introducer sheath hub 440 that is coupled to and disposed generally proximal of the tubular member 432. The introducer sheath hub 440 may include wings 444 that extend radially away from a longitudinal axis of the introducer sheath hub 440 and a female luer lock fitting 442 adjacent the proximal end of the introducer sheath hub 440. In the depicted embodiment, the female luer lock fitting 442 does not threadably engage with the dilator hub 420, as the dilator hub 420 does not include threads for mating with the female luer lock fitting 442.

The dilator 410 may be inserted within and coupled to the introducer sheath 430 as shown in FIG. 4C. For example, the distal end of the dilator 410 may be inserted through a proximal opening of the introducer sheath 430 and advanced within the introducer sheath 430. As the dilator 410 is advanced within the introducer sheath 430, the finger input portions 462 may be pressed toward one another, thereby causing the cylindrical member 425 to transition from an unconstrained configuration (e.g., FIG. 4F) to a constrained configuration (e.g., FIG. 4G).

As the cylindrical member 425 transitions from an unconstrained to a constrained configuration, the shape of the cylindrical member 425 may be altered. For example, constraining the cylindrical member 425 may cause a cross-section of the cylindrical member 425, such as that shown in FIGS. 4F and 4G, to become less oblong. Stated differently, when the cylindrical member 425 is in a constrained configuration (see, e.g., FIG. 4G), a plane that is perpendicular to the longitudinal axis of the cylindrical member 425 may intersect the cylindrical member 425 to form a shape that is less oblong than the shape formed by the intersection of the same plane with the cylindrical member 425 when the cylindrical member 425 is in an unconstrained configuration (see, e.g., FIG. 4F). For example, in some embodiments, a cross-section of the cylindrical member 425 may become more circular in shape as the finger input portions 462 are pressed toward one another.

Due to the changing shape of the cylindrical member 425 and the radial offset of the finger input portions 462 from the one or more protrusions 480, pressing the finger input portions 462 toward one another may cause the one or more protrusions 480 to be displaced radially outward from a longitudinal axis of the dilator 410 (compare FIGS. 4F and 4G). Such radial displacement of the one or more protrusions 480 may allow a proximal portion of the introducer sheath hub 440 (e.g., the female luer lock fitting 442) to extend past at least one protrusion 480. Once the female luer lock fitting 442 is positioned within the cylindrical member 425 such that the protuberance 424 is in contact with an inner surface of the introducer sheath hub 440, the practitioner may cease to provide input to the finger input portions 462, thereby allowing the finger input portions 462 to revert to an unconstrained configuration in which the one or more protrusions 480 engage the female luer lock fitting 442, thereby coupling the dilator hub 420 to the introducer sheath hub 440. In an analogous manner, the dilator hub 420 can more generally couple to other connectors that include an annular ridge or circular portion at or adjacent to one end.

In some embodiments, the process of inserting the dilator 410 into the introducer sheath 430 and coupling the dilator 410 to the introducer sheath 430 may be accomplished (1) without rotating the dilator hub 420 relative to the introducer sheath hub 440, and/or (2) by a mechanism that does not involve an interaction between threads on the dilator hub 320 and threads on the introducer sheath hub 340.

Once the dilator 410 has been coupled to the introducer sheath 430, a portion of the introducer sheath assembly 400 may be percutaneously inserted into a patient in a manner analogous to that described above in connection with other introducer sheath assemblies.

Once the introducer sheath 430 of the introducer sheath assembly 400 has been properly positioned within the patient, the dilator 410 may be uncoupled from the introducer sheath 430 and withdrawn from the introducer sheath 430. In some instances, such a process essentially reverses the steps described above for inserting the dilator 410 into the introducer sheath 430 and coupling the dilator 410 to the introducer sheath 430. For example, a practitioner may press the finger input portions 462 toward one another, thereby causing the one or more protrusions 480 of the cylindrical member 425 to be radially displaced. Once the one or more protrusions 480 have been radially displaced, the practitioner may withdraw the dilator 410 from the introducer sheath 430. In this manner, the dilator hub 420 may be single-handedly uncoupled from the introducer sheath hub 440 without rotating the dilator hub 420 relative to the introducer sheath hub 440. Further, the dilator hub 420 and the introducer sheath hub 440 may be coupled and uncoupled from one another by a process that does not involve threads.

While the hubs and hub assemblies disclosed herein are described above with reference to introducer sheath assemblies that include a dilator and an introducer sheath, the hubs disclosed herein—such as hubs 210, 230, 310, 330, 410, and 430—may be used in many other medical contexts. For example, hubs disclosed herein may be used to couple any suitable medical device or medical device component to another medical device or medical device component. More particularly, the hubs 210, 230, 310, 330, 410, and/or 430 may be used, for example, to couple a medical tube, a catheter, a needle, a trocar, etc. to any other medical device or medical device component. For example, the hubs 210, 230, 310, 330, 410, and/or 430 may facilitate coupling of a first medical tube to a second medical tube. In many instances, the hubs disclosed herein may be used in lieu of standard luer fittings.

Any methods disclosed herein include one or more steps or actions for performing the described method. The method steps and/or actions may be interchanged with one another. In other words, unless a specific order of steps or actions is required for proper operation of the embodiment, the order and/or use of specific steps and/or actions may be modified. Moreover, sub-routines or only a portion of a method described herein may be a separate method within the scope of this disclosure. Stated otherwise, some methods may include only a portion of the steps described in a more detailed method.

Reference throughout this specification to "an embodiment" or "the embodiment" means that a particular feature, structure, or characteristic described in connection with that embodiment is included in at least one embodiment. Thus, the quoted phrases, or variations thereof, as recited throughout this specification are not necessarily all referring to the same embodiment.

Similarly, it should be appreciated by one of skill in the art with the benefit of this disclosure that in the above description of embodiments, various features are sometimes grouped together in a single embodiment, figure, or description thereof for the purpose of streamlining the disclosure. This method of disclosure, however, is not to be interpreted as reflecting an intention that any claim requires more features than those expressly recited in that claim. Rather, as the following claims reflect, inventive aspects lie in a combination of fewer than all features of any single foregoing disclosed embodiment. Thus, the claims following this Detailed Description are hereby expressly incorporated into this Detailed Description, with each claim standing on its own as a separate embodiment. This disclosure includes all permutations of the independent claims with their dependent claims.

Recitation in the claims of the term "first" with respect to a feature or element does not necessarily imply the existence of a second or additional such feature or element. It will be apparent to those having skill in the art that changes may be made to the details of the above-described embodiments without departing from the underlying principles of the present disclosure.

The invention claimed is:

1. An introducer sheath assembly comprising:
   an introducer sheath comprising:
      a first tubular member configured to be at least partially inserted into a patient, the first tubular member at least partially defining a lumen that extends therethrough; and
      an introducer sheath hub coupled to the first tubular member and disposed adjacent the proximal end of the first tubular member, wherein the introducer sheath hub comprises a first semi-annular ridge, a second semi-annular ridge disposed circumferentially less than 180 degrees from the first semi-annular ridge, and a semi-annular opening disposed on a perimeter of the introducer sheath hub between the first and second semi-annular ridges; and
   a dilator comprising:
      an elongate shaft that is configured to be at least partially disposed within the lumen that extends through the first tubular member, the elongate shaft defining a longitudinal axis; and
      a dilator hub coupled to the elongate shaft and disposed adjacent a proximal end of the elongate shaft, wherein the dilator hub is configured to selectively couple to the introducer sheath hub without rotating the dilator hub relative to the introducer sheath hub, the dilator hub comprising a first semi-annular input portion and a second semi-annular input portion disposed opposite of the first semi-annular input portion and connected to the dilator hub,
   wherein the first semi-annular input portion comprises at least one distally extending catch disposed at a perimeter of the first semi-annular input portion,
   wherein the at least one distally extending catch is disposed through the opening and engaged with the first semi-annular ridge when the dilator hub is coupled to the introducer sheath hub, wherein deflection of the first input portion toward the second input portion causes the at least one catch to deflect tangentially to the perimeter of the first semi-annular input portion, and wherein the deflection of the first input portion causes the at least one catch to disengage from the first semi-annular ridge of the introducer sheath hub.

2. The introducer sheath assembly of claim 1, wherein the dilator hub is configured to couple to the introducer sheath hub via a snap-fit connection.

3. The introducer sheath assembly of claim 1, wherein the dilator hub is configured to facilitate single-handed uncoupling of the dilator hub from the introducer sheath hub.

4. The introducer sheath assembly of claim 1, wherein the introducer sheath hub comprises external threads, and wherein the dilator hub is configured to couple and uncouple from the introducer sheath hub via a mechanism that does not involve an interaction with the external threads.

5. The introducer sheath assembly of claim 1, wherein the introducer sheath assembly provides audible feedback when the introducer sheath assembly transitions from a configuration in which the dilator hub is uncoupled from the introducer sheath hub to a configuration in which the dilator hub is coupled to the introducer sheath hub.

6. The introducer sheath assembly of claim 1, wherein the introducer sheath assembly comprises a positive stop that is visually observable when the dilator hub is coupled to the introducer sheath hub.

7. The introducer sheath assembly of claim 1, wherein the introducer sheath hub comprises a female luer lock fitting.

8. The introducer sheath assembly of claim 1, wherein the dilator hub comprises:

wherein the first semi-annular input portion and the second semi-annular input portion are configured to facilitate uncoupling of the dilator hub from the introducer sheath hub when pressed toward one another.

9. The introducer sheath assembly of claim 8, wherein the dilator is configured to be inserted into the introducer sheath such that the dilator hub couples to the introducer sheath hub without applying an external force directly to the first semi-annular input portion or the second semi-annular input portion.

10. An introducer sheath assembly comprising:
an introducer sheath comprising:
a first tubular member configured to be at least partially inserted into a patient, the first tubular member at least partially defining a lumen that extends therethrough; and
an introducer sheath hub coupled to the first tubular member and disposed adjacent the proximal end of the first tubular member, wherein the introducer sheath hub comprises at least two semi-annular ridges, wherein a first semi-annular ridge is disposed circumferentially less than 180 degrees from a second semi-annular ridge; and
a dilator comprising:
an elongate shaft that is configured to be at least partially disposed within the lumen that extends through the first tubular member, the elongate shaft defining a longitudinal axis; and
a dilator hub coupled to the elongate shaft and disposed adjacent a proximal end of the elongate shaft, wherein the dilator hub is configured to selectively couple to the introducer sheath hub without rotating the dilator hub relative to the introducer sheath hub, the dilator hub comprising at least two semi-annular input portions connected to the dilator hub, wherein the at least two input portions comprise at least one distally extending catch disposed at a distal perimeter of the at least two semi-annular input portions, wherein the at least one catch is configured to at least partially pass through an opening between the first and second semi-annular ridges and engage with at least one semi-annular ridge to couple the dilator hub to the introducer sheath hub, and wherein deflection of the at least two input portions toward the longitudinal axis of the elongate shaft causes the at least one catch of the at least two input portions to deflect tangentially to the perimeter of the at least two semi-annular input portions.

11. An introducer sheath assembly comprising:
an introducer sheath comprising:
a first tubular member configured to be at least partially inserted into a patient, the first tubular member at least partially defining a lumen that extends therethrough; and
an introducer sheath hub coupled to the first tubular member and disposed adjacent the proximal end of the first tubular member, wherein the introducer sheath hub comprises a first semi-annular ridge and a second semi-annular ridge disposed circumferentially less than 180 degrees from the first semi-annular ridge; and
a dilator comprising:
an elongate shaft that is configured to be at least partially disposed within the lumen that extends through the first tubular member, the elongate shaft defining a longitudinal axis; and
a dilator hub coupled to the elongate shaft and disposed adjacent a proximal end of the elongate shaft, wherein the dilator hub is configured to selectively couple to the introducer sheath hub without rotating the dilator hub relative to the introducer sheath hub, the dilator hub comprising at least one semi-annular input portion connected to the dilator hub, wherein the at least one semi-annular input portion comprises a perimeter and at least one distally extending catch disposed on the perimeter, wherein the at least one distally extending catch is circumferentially offset from the at least one semi-annular input portion, wherein deflection of the at least one input portion toward the longitudinal axis of the elongate shaft causes the at least one catch to deflect tangentially to the perimeter of the at least one semi-annular input portion, and wherein the deflection of the at least one input portion causes the at least one catch to disengage from at least one semi-annular ridge of the introducer sheath hub.

* * * * *